United States Patent [19]

Widder

[11] Patent Number: 5,373,846
[45] Date of Patent: Dec. 20, 1994

[54] METHOD OF ULTRASONIC IMAGING OF BODY CAVITIES

[75] Inventor: Kenneth J. Widder, Del Mar, Calif.

[73] Assignee: Molecular Biosystems, Inc., San Diego, Calif.

[21] Appl. No.: 142,653

[22] Filed: Oct. 25, 1993

Related U.S. Application Data

[63] Continuation of Ser. No. 957,215, Oct. 6, 1992, abandoned.

[51] Int. Cl.$^5$ ............................................. A61B 8/00
[52] U.S. Cl. ............................................. 128/662.02
[58] Field of Search ............... 128/660.01, 662.02, 128/660.07; 424/4

[56] References Cited

U.S. PATENT DOCUMENTS

| | | | |
|---|---|---|---|
| 4,324,849 | 4/1982 | Kerr et al. | 128/660.01 |
| 4,681,119 | 7/1987 | Rasor et al. | 128/662.02 |
| 4,774,958 | 10/1988 | Feinstein | 128/660.01 |
| 4,844,882 | 7/1989 | Widder et al. | 128/660.01 |
| 4,957,656 | 9/1990 | Cerny et al. | 128/662.02 |
| 5,107,842 | 4/1992 | Levene et al. | 128/662.02 |
| 5,179,955 | 1/1993 | Levene et al. | 128/662.02 |
| 5,196,183 | 3/1993 | Yadelson et al. | 128/662.02 |

FOREIGN PATENT DOCUMENTS

91/18612 12/1991 WIPO ............... 128/660.01

OTHER PUBLICATIONS

Ophir et al., Ultrasound in Med. & Biol., 15:319–333 (1989).
Keller et al., Amer. Hear J., 114:570–575 (1987).
Weighall, et al., J. Clin. Ultrasound, 7:353–356 (1979).
Warren et al., J. Clin. Ultrasound, 6:315–320 (1978).
Stringer et al., J. Clin. Ultrasound, 5:183–188 (1986).
Worlicek et al., J. Clin. Ultrasound, 17:5–14 (1989).
Op den Orth, curr. Opin. Radiol., 2:394–399 (1990).

*Primary Examiner*—George Manuel
*Attorney, Agent, or Firm*—Morrison & Foerster

[57] ABSTRACT

The ultrasound imaging of body cavities and surrounding organs is carried out by introducing into the body cavity an aqueous solution of water-soluble hydrocolloid. The hydrocolloid solution is homogeneous, has a viscosity of 200 to 800 cp at 25° C., and is free of gas bubbles and ultrasound-reflecting solid particles. The introduction of the solution into the cavity displaces air therefrom, and while the solution is retained in the cavity an ultrasonic imaging beam is applied to obtain an imaging contrast in which the solution appears sonolucent, that is, essentially black against the more sonoreflective body tissues and organs.

14 Claims, No Drawings

METHOD OF ULTRASONIC IMAGING OF BODY CAVITIES

This application is a continuation, of application Ser. No. 07/957,215, filed Oct. 6, 1992 now abandoned.

FIELD OF INVENTION

This invention relates to ultrasonic imaging of the human body for diagnostic purposes; and, more particularly, to ultrasonic imaging of externally-accessible body cavities and to contrast media for use therein.

BACKGROUND OF INVENTION

An examination procedure known as ultrasonography or sonography is used clinically to delineate body structures by ultrasonic imaging. Progress and practical applications of diagnostic ultrasonic imaging have been delayed by lack of effective clinically usable contrast agents. This has especially been the situation for ultrasonic imaging of air-containing, externally-accessible body cavities, such as the gastrointestinal (GI) tract, uterus, and bladder.

Ultrasonic imaging utilizes an ultrasonic scanner to generate and receive sound waves. The scanner is placed on a body surface overlying the area to be imaged, and sound waves are directed toward that area. The scanner detects reflected sound waves and translates that data into images. When ultrasonic energy propagates through an inhomogeneous substance, the acoustic properties of the substance determine the degree of absorption, scattering, and transmission of the ultrasound. As ultrasound waves propagate through one medium to another, there is some degree of reflection at the interface. The degree of reflection is related to the acoustic properties of each material.

Contrast agents for diagnostic ultrasound were reviewed by Ophir and Parker, *Ultrasound in Med. & Biol.* (1989), 15:319–333. Various contrast agents were described for intravascular administration and imaging. These included free and encapsulated gas bubbles, colloidal suspensions, emulsions, and aqueous solutions. Mechanisms which can enhance image contrast are discussed, including backscatter contrast, attenuation contrast, and speed of sound contrast. The authors observed that the development of image-enhancing agents "has been slow and sporadic, and to date there are no completely satisfactory materials for clinical imaging." In a concluding paragraph, the authors added: "The clinical need for ultrasound contrast agents is high, but much interdisciplinary research, covering acoustic material properties, imaging, biochemistry, histology, toxicology and related specialties will be required before ultrasound contrast agents are commercially available and in routine clinical use."

With reference to encapsulated gas bubbles as ultrasonic imaging agents for intravascular administration, Ophir and Parker (1989), cited above, stated that feasibility remained uncertain because sufficiently stable bubbles of a size permitting administration in the peripheral circulation had not been developed. This was first accomplished by an invention of Dr. Steven B. Feinstein, as described in U.S. Pat. No. 4,774,958. By the sonication of an aqueous solution of human albumin, encapsulated microbubbles of relatively uniform size in the 2 to 5 micron range can be produced. The resulting imaging agent can pass through capillaries, and therefore can be administered in a peripheral vein for heart imaging, as reported by Keller, Feinstein, and Watson (1987), *Amer. Heart J.*, 114:570–575. A concentrated shelf-stable microbubble imaging agent of this kind can be prepared as described in U.S. Pat. Nos. 4,844,880, and 4,957,656 assigned to Molecular Biosystems, Inc.

More recently, Molecular Biosystems has carried out research on imaging agents and methods for enhancing ultrasonic imaging of the gastrointestinal (GI) tract. This research was initially directed to particulate imaging agents, as described in U.S. Pat. No. 5,107,842, based on application Ser. No. 660,349, filed Feb. 22, 1991. Particulate ultrasonic imaging agents for the GI tract are also described in PCT Application WO 91/18612, published Dec. 12, 1991.

Heretofore, in development of ultrasonic contrast agents, principal emphasis has been directed to the contrast media containing dispersed air bubbles or solid particles, which reflect ultrasound and produce backscatter. These media function primarily as "positive" sonoreflective contrast agents, appearing light in the ultrasonic image rather than dark. Ultrasonic evaluation of body cavities is sometimes carried out in the absence of a positive contrast agent which, if present, would obscure the clarity of surrounding organ structures. However, even in the absence of a positive contrast agent, problems are encountered when there are substances within the body cavities which reflect sound. In order to overcome this problem, several authors have described the introduction of media into the body cavity through which the surrounding organs and tissues can be visualized. This method has achieved only limited success.

Weighall, et al. (1979), *J. Clin. Ultrasound*, 7:353–356, describe that "gastric air and peristalsis usually are obstacles to the ultrasound imaging of the tail of the pancreas"; and "air within the stomach drastically attenuates the transmission of ultrasound". The result is that "the stomach is a hinderance to ultrasound imaging of the organs of the left upper quadrant of the abdomen." In order to overcome this difficulty, the authors describe the use of intravenous glucagon to slow down peristalsis in conjunction with the ingestion of water to displace air. This method was not entirely satisfactory, since it did not result in the removal of all of the interfering microbubbles and food debris within the stomach which produced backscatter and appeared white in the ultrasonic images.

Warren, et al. (1978) *J. Clin. Ultrasound*, 6:315–320, describes the formation of an "ultrasonic window" by using a liquid-filled stomach. A mucilaginous suspension of methylcellulose was administered in conjunction with an intravenous injection of Buscopan to slow peristalsis. The authors report that the suspension "allows good through-transmission of sound", but the photographs presented in the article demonstrate that the clumped methylcellulose mucilages appear as white granular sonoreflective bodies (positive contrast) in the ultrasonic images. The presence of the mucilages would thus limit the usefulness of this procedure for ultrasonic imaging of the upper abdomen.

For sonographic examination of childrens' stomachs, Stringer et al. (1986), *J. Ultrasound Med.*, 5:183–188, used water with added glucose.

Worlicek et al. (1989), *J. Clin. Ultrasound*, 17:5–14, describes the ultrasonic imaging of the gastrointestinal tract after having the patient ingest a significant quantity of orange juice in conjunction with an intravenous injection of Buscopan . The success of this procedure depends largely on the positioning of the patient during the examination due to the presence of air in the gastrointestinal tract. The authors describe that "the air, which completely reflects ultrasonic waves, is removed from the section of the stomach under investigation by appropriate positioning."

Current progress in transabdominal ultrasonography of the stomach and duodenum was reviewed by Op den Orth, *Curr. Opin. Radiol.* (1990), 2:394–399. Published research was summarized on the examination of the stomach wall with the aid of fluid media. In the conclusion, the authors note that a tilting table is essential for patient positioning during the ultrasonic examination. They also note that, "Even with this type of table, however, the fundus is sometimes difficult to examine."

There thus exists a need for a contrast agent which permits through-transmission of ultrasound with negligible reflection or back-scatter, and therefore appears black in contrast to the whiter appearing surrounding tissue, i.e., a "negative" contrast agent. Such a contrast agent which facilitates the removal of gas in the body cavities is necessary for clinically successful ultrasonic examination of the body cavity tissues and surrounding organs which may be hampered by the presence of echogenic substances.

SUMMARY OF INVENTION

This invention provides a method of imaging externally-accessible body cavities by employing viscous aqueous solutions. The method achieves maximized beam penetration without backscatter and thus provides a negative contrast when compared to surrounding tissues and organs.

The media comprise aqueous homogeneous solutions of hydrocolloids, which provide the solutions with viscosities in the range from 200 to 800 centipoise (cp). The solutions are free of gas bubbles and ultrasound reflecting solid particles.. These media are useful in ultrasonic examination of the walls or surrounding tissues or organs of body cavities, including but not limited to the stomach, the upper and lower gastrointestinal tract, the uterus and the bladder.

The solubilized hydrocolloid media of this invention are distinguished from aqueous suspensions of particulate hydrocolloids which are used as positive contrast agents. (See U.S. Pat. No. 5,107,842 and PCT WO 91/186212, cited above.) The use of particulate hydrocolloids as positive contrast agents is due to their ability to reflect ultrasonic waves producing backscatter. Such particulate-type media can be employed to coat the stomach or upper GI, which are imaged after the bulk of the medium has moved out of the region being examined. This results in the image of the stomach or upper GI being enhanced, or whitened, by the presence of the particulate-type contrast media.

The differing method of the present invention is based on the discovery that homogeneous solutions of certain hydrocolloids do not reflect ultrasound and can be utilized as negative contrast agents. In the ultrasonic image, these agents provide a "black against white" contrast, with the contrast media in the body cavity appearing "black", while the body cavity walls, surrounding tissues and organs appear "white". Such a contrast media can be referred to as being sonolucent (transparent to sound), that is, free of ultrasound reflecting and attenuating substances such as particles and gas.

When used in accordance with the method of this invention, the viscous hydrocolloid solutions provide important advantages. By having the medium essentially free of gas bubbles prior to administration, the amount of ingested air which would produce backscatter is minimized. Additionally, when ingested or infused into the body cavity, air which is present in the body cavity is displaced. The highly viscous nature of the media allows displacement of air while minimizing intermixing of the displaced air with the contrast media, which if allowed to occur would result in the dispersion of air and microbubble formation within the contrast media. The viscosity of the medium also tends to promote its retention in the body cavity, thereby lengthening the time period in which examinations can be carried out.

DETAILED DESCRIPTION

The contrast media for practicing the method of this invention are prepared by dissolving hydrocolloids in water, such as distilled sterile water. The water should be free of solid particles or dissolved substances which might form solid particles that would reflect ultrasonic waves. The media should be prepared with appropriate concentrations of the hydrocolloid to form a highly viscous solution while maintaining the sonolucent character of the media.

It is important to employ a hydrocolloid which forms a homogenous solution when dissolved in water. Hydrocolloids which form dispersions containing particles larger than 50 microns should be avoided. A hydrocolloid should be selected which can be dissolved or dispersed in water to form either a true solution or an ultrafine dispersion. Hydrocolloids which are essentially water-soluble, such as pectin, are preferred, but other hydrocolloids can be used. These include but are not limited to xanthan, sodium alginate, propylene glycol alginate and carrageenan.

Hydrocolloids are commonly supplied as dry powders. Pectins and some other hydrocolloids are commercially available in a form which is readily soluble in water. Ordinary mixing of the water with the hydrocolloid at room temperature (20°–25° C.) can then be used to produce the desired negative contrast media. If more rapid solubilization of a hydrocolloid is desired, it can be dry blended with sugar (sucrose). Further, heating can be applied to the mixture as needed. For example, a mixture of water and the hydrocolloid can be boiled for 1–2 minutes.

The suitability of a hydrocolloid for purpose of the present invention can be determined by preparing admixtures with water within the range from 0.5 to 8% by weight. The amount of the hydrocolloid used should provide a solution viscosity in the range of 200 to 800 centipoise (cp) at 25° C. and preferably from 300 to 600 cp at 25° C. For example, pectin can be employed in amounts of 2 to 5% by weight. In a preferred embodiment, the pectin percent is from 3 to 4% and provides viscosities of from 520 to 575 cp. The suitability of a prepared solution can be confirmed by determining that it is essentially as sonolucent as water.

A homogeneous solution of the hydrocolloid as prepared above should be relatively free of gas bubbles. It is preferably subjected to degassing to remove air or other gas bubbles. For example, a reduced pressure (vacuum) degassing chamber can be used.

EXPERIMENTAL STUDY

The experimental basis of the negative contrast media of this invention is illustrated by the following study.

A. Data Acquisition

The negative contrast agents were formed according to the following general method. A 3 to 10% (w/v) solution of the hydrocolloid was prepared in distilled water. The pectin (or other hydrocolloid) was added to the water in a Waring blender and mixed for 5 minutes. (Preservatives, sweeteners, or flavorings could be added, but were not used in this study.) The mixtures were allowed to sit for 5 minutes after any foam that has accumulated in the mixing process was removed. (If required to obtain a homogeneous solution, the mixtures can be boiled for one minute and then cooled to room temperature, but this was not used with the samples described below.) Degassing of the solution was attained in a vacuum degassing chamber. After the solutions were free of entrapped air bubbles, ultrasound analysis was performed.

A Hewlett-Packard Sonos 100 Ultrasound Imaging instrument was used in B mode to detect the scattering or non-scattering capability of the sample solutions. Pure water was used as a negative contrast reference standard. Coupling gel and absorption pads were placed beneath the bottles to minimize reflection artifacts. While imaging the water standard, the time-gain compensation controls were set so that the water appeared black. Other experimental parameters included use of a 3.5 or 5 MHz transducer and a display depth of 4 to 8 cm. The ultrasound signals for water and the sample mixtures were video recorded under identical experimental conditions.

B. Data Analysis

The recorded ultrasound signal was digitized with an Apple Macintosh II Computer using "CineProbe" image processing software. The video signal was monitored on the Macintosh screen from which a video frame showing an image sector was selected. Within the image sector, an area of 20,000 pixels (approximately 25% of the image sector) was chosen and the mean density (MD) or average grey scale was determined for this area. This mean density (MD) scale was correlated with water, which gave an MD of 252–256.

C. Results

The results of the study are summarized below in Table A.

TABLE A

| Sample | Manufacturer | Conc. % (wt./vol) | Viscosity* (cp) | Mean Density (MD) |
| --- | --- | --- | --- | --- |
| Sterile DI water | Aerohead | — | — | 253.96 |
| Pectin LM-32 | TIC GUMS, INC. | 3.50% | 524 | 253.10 |
| Genu Pectin USP L-200 | Hercules, Inc. | 3.75% | 571 | 253.90 |
| Xanthan PH (xanthan gum) | TIC GUMS, INC. | 0.51% | 426 | 253.90 |
| Keltrol T (xanthan gum) | Kelco | 0.80% | 434 | 253.17 |
| Kelgin F (sodium alginate) | Kelco | 1.46% | 449 | 253.85 |
| Kelgin MV (sodium alginate) | Kelco | 1.40% | 551 | 253.94 |
| Keltone HV (sodium alginate) | Kelco | 1.16% | 541 | 253.92 |
| Colloid 602 (propylene glycol alginate) | TIC GUMS, INC. | 1.55% | 498 | 253.89 |
| Colloid 720 (carageenan) | TIC GUMS, INC. | 1.13% | 384 | 253.91 |
| Colloid 775 (carageenan) | TIC GUMS, INC. | 0.90% | 491 | 253.03 |

*Viscosity measured at room temperature (20–25° C.).

The contrast media of the foregoing study contained only distilled water and the designated hydrocolloid. However, in commercial embodiments, other ingredients may be included, such as ingredients to improve palatability. For example, the solutions may contain dissolved sweeteners and/or flavoring agents. Soluble degassing agents such as simethicone may be included but are not seen to be needed. For introduction into a body cavity, the solution should be in sterile form. After preparation, the solution can be subjected to sterilization by heating or by subjecting it to gamma irradiation. Procedures should be avoided which tend to agglomerate or gel the solutions. The solutions should remain fluid and the formation of sonoreflective particulates should be avoided.

The media prepared as described will have essentially the same "blackness" value (MD) as water, indicating that they are transparent to ultrasonic waves being essentially sonolucent. Preferably, the solutions have an ultrasound mean density (MD) of 250 or higher on a scale where water has an MD of 252 to 256.

Depending on the body cavity to be examined, the media solutions may be administered orally or by infusion. The body cavities that may be examined include the gastrointestinal tract, or more specifically, the stomach, the duodenum, upper gastrointestinal tract, or the lower gastrointestinal tract. For the stomach and upper gastrointestinal tract, oral administration can be employed. Introduction into the stomach by means of a tube can also be used. For the lower GI tract, the media can be administered by enema. Infusion administration can also be used for intra-uterine administration. Administration through a catheter can be employed for bladder examination. From 100 to 1000 milliliters of the media can be used. For example, for examination of the stomach or duodenum, the patient can be instructed to drink amounts of the solution which are sufficient to fill the stomach, such as 0.5 liters.

Ultrasonic imaging can be carried out by standard procedures using commercially available equipment. The frequency of the ultrasonic beam can be varied, for example, from 1 to 10 MHz. Typical frequencies, such as for imaging the stomach, or other examination of the gastrointestinal tract, will usually range from about 3 to 5 MHz. Because of the viscosity of the solutions, they will persist in the cavity to be examined for a sufficient period of time to permit the examination. For example, examinations can be carried out within 5 to 20 minutes after administration.

Clinical procedures for examining body cavities can be varied by the sonographer, as required for detecting specific pathologic conditions. The following general procedures are illustrative.

Stomach—Upper GI 150 to 500 ml of the 3.5% pectin solution (degassed) is ingested over a two minute period. Ultrasonic examination of the stomach and duodenum using a 5 MHz transducer reveals an immediate cloud of sonoreflective signal upon entry of the contrast material into the stomach. This cloud of positive signal represents entrapped air in the esophagus being pushed into the stomach by the leading edge of the contrast material.

Within five minutes after ingestion, the stomach becomes dilated due to the volume ingested with the disappearance of substantially all the air visualized initially, leaving the stomach cavity "black" (negative contrast) and highlighting the positive or "white" border of the GI wall. This negative contrast effect remains visible in the ultrasonic image for up to 30 minutes after ingestion depending on the volume ingested. As the contrast material moves into the upper GI tract, the negative contrast effect can be appreciated. Because of the excellent through transmission properties of the contrast material, structures distal to the stomach, such as the pancreas, can be significantly visually enhanced.

Uterus 1.5 to 3 cc of the negative contrast material can be injected via a catheter into the uterus through the cervical os. The material expands the endometrial cavity and significantly enhances the ability to discriminate the shape of the endometrium.

Lower GI 150 to 300 cc of the contrast material can be administered as an enema to disperse and facilitate ultrasound examination of the lower GI.

I claim:

1. A method of ultrasound imaging of an externally-accessible body cavity, comprising introducing into the body cavity to be examined an aqueous solution of a hydrocolloid, said solution being homogenous, having a viscosity of 200 to 800 cp at 25° C., being free of ultrasound reflecting particles and essentially sonolucent, the introduction of said solution into said cavity displacing air therefrom, and while said solution is retained in said cavity applying an ultrasonic imaging beam to said cavity to obtain an imaging contrast.

2. The method of claim 1 in which said body cavity is a part of the gastrointestinal tract.

3. The method of claim 1 in which said body cavity is the stomach.

4. The method of claim 1 in which said body cavity is the upper gastrointestinal tract.

5. The method of claim 1 in which said body cavity is the uterus.

6. The method of claim 1 in which said body cavity is the bladder.

7. The method of claims 1, 2, 3, 4, 5 or 6 in which said solution has hydrocolloid concentration within the range from 0.5 to 8% by weight which provides a solution viscosity of 300 to 600 cp.

8. The method of claims 1, 2, 3, 4, 5 or 6 in which said hydrocolloid is water-soluble pectin at a concentration of 2 to 5% by weight.

9. The method of claims 1, 2, 3, 4, 5 or 6 in which the imaging contrast blackness of said solution is indistinguishable from the imaging contrast blackness of deareated particle-free water.

10. The method of claims 1, 2, 3, 4, 5 or 6 in which said solution has an ultrasound mean density (MD) of at least 250 on a scale where water has a MD of 252 to 256.

11. A method of ultrasound imaging of an externally-accessible body cavity, comprising introducing into the body cavity to be examined an aqueous solution of a hydrocolloid, said solution containing from 0.5 to 8% by weight of said hydrocolloid, said hydrocolloid being present in a sufficient concentration to provide a viscosity of 300 to 600 cp at 25° C., said solution being further characterized as homogenous, free of ultrasound reflecting particles, and essentially sonolucent, the introduction of said solution into said cavity displacing air therefrom, and while said solution is retained in said cavity applying an ultrasonic imaging beam to said cavity to obtain an imaging contrast.

12. The method of claim 11 in which the imaging contrast blackness of said solution is indistinguishable from the imaging contrast blackness of deareated particle-free water.

13. The method of claim 11 in which said solution has an ultrasound mean density (MD) of at least 250 on a scale where water has a MD of 252 to 256.

14. The method of claims 11, 12 or 13 in which said hydrocolloid is water-soluble pectin.

* * * * *